United States Patent [19]

Tsujii et al.

[11] 3,955,086
[45] May 4, 1976

[54] RADIATION THICKNESS GAUGE

[75] Inventors: Tatsuo Tsujii, Tokyo; Fumio Nishiwaki, Kawasaki, both of Japan

[73] Assignee: Tokyo Shibaura Denki Kabushiki Kaisha, Kawasaki, Japan

[22] Filed: May 6, 1975

[21] Appl. No.: 574,875

[30] Foreign Application Priority Data
May 13, 1974 Japan.............................. 49-52324

[52] U.S. Cl............................. 250/358 R; 250/252; 250/359
[51] Int. Cl.²........................................ G01N 23/00
[58] Field of Search ............ 250/252, 358, 359, 360

[56] References Cited
UNITED STATES PATENTS

| | | | |
|---|---|---|---|
| 3,334,230 | 8/1967 | Shaffer................................ | 250/252 |
| 3,611,408 | 10/1971 | Shoemaker et al. ............. | 250/252 X |

*Primary Examiner*—Davis L. Willis
*Attorney, Agent, or Firm*—Stevens, Davis, Miller & Mosher

[57] ABSTRACT

In a radiation thickness gauge of the type wherein the thickness of a sample is determined by measuring the amount of radiations transmitting through the sample, there is provided an x-ray generator for transmitting a radiation flux through a reference sheet utilized for calibration purposes and having a thickness manifesting a radiation absorption which is equivalent to that of the sample having a nominal thickness which has been compensated for the difference in the radiation absorption characteristics of the reference sheet and the sample, a radiation detector for detecting the amount of the radiations transmitting through the reference sheet and the sample, a memory for storing the output of the detector when the reference sheet is interposed, and an operator, such as a computer. The operator functions to substitute the output of the radiation detector when the sample is interposed for a term representing the variation in the thickness of an equation determined by the content of the memory and the radiation absorption function of the reference sheet so as to produce an output signal representing the thickness of the sample.

9 Claims, 2 Drawing Figures

RADIATION THICKNESS GAUGE

BACKGROUND OF THE INVENTION

This invention relates to an improvement of a thickness gauge wherein the thickness of sheets of various materials is measured by measuring the amount or intensity of the radiations transmitting through the sheets.

Thickness gauges of this type have been used extensively in various applications because it is possible to continuously measure the thickness of web shaped material without contacting the same. Especially, where a source of X-rays is utilized as the radiation source, since the noise caused by the radiations is small and since the response is fast, X-ray radiation gauges are widely used for on line measurement in rolling mill lines of metals, such as steel and aluminum and for the automatic adjustment of the gauge.

However, in the prior art X-ray thickness gauge the attenuation characteristic of the substance varies in accordance with the energy of the X-ray generator or the radiation source, so that the variation with time in the output of the X-ray generator, that is the so-called drift causes errors in the measured value of the sheet gauge. Moreover, the sensitivity of the detector and the constants of the associated electrical circuits also vary due to aging and variation in the external conditions and these variations also cause errors in the measured value.

According to a prior art thickness gauge shown in FIG. 1, for the purpose of improving the measuring accuracy, a reference sheet 11 is provided which is used to calibrate the thickness gauge each time the measurement is made. More particularly, a preset signal is applied to a gauge setting device 12 and a gauge correction device 13 so that an operator or an electronic computer 14 performs an operation in accordance with an equation which determines a reference sheet having an amount of absorption of the radiations which is equivalent to the thickness of a sheet or sample to be measured, thus applying a control signal to driving means 15 for inserting the reference sheet corresponding to the input signal across the X-ray flux radiated from a X-ray generator 21. The X-rays attenuated by the reference sheet are received by a radiation detector 16 for producing an electric signal which is converted into a signal proportional to the thickness of the reference sheet by the action of a non-linear amplifier 17. The output from this amplifier is compared with the output of the gauge setting device 12 in a comparator 18 and the output thereof is applied to an indicating meter 19 through an amplifier 20. Further, a servo-system 10 is provided for driving a member (not shown) for varying the energy of the X-rays generated by the X-ray generator 21 or a member (not shown) for adjusting the intensity of the X-rays as shown by dotted lines, thus calibrating the X-ray gauge meter. Thereafter, a sheet to be measured 22 is inserted across the X-ray flux instead of the reference sheet 11 for measuring the thickness of the sheet 22.

However, in the radiation thickness gauge just described since the operation parameters of the thickness gauge are adjusted to a calibrated state by the servo-system for providing the zero point calibration as well as the sensitivity calibration the adjustment of the operation parameters by the servo-system causes errors in the measured thickness.

SUMMARY OF THE INVENTION

Accordingly, it is an object of this invention to provide an improved radiation thickness gauge capable of measuring the thickness of a sheet at high accuracies without using any servo-system and without accompanying the difficulties described above.

Another object of this invention is to provide an improved radiation gauge whose measuring accuracy is not affected by the difference in the radiation energy and the radiation intensity at the times of measurement and calibration.

A further object of this invention is to provide an improved radiation thickness gauge which is easy to use and can display the measured thickness as digital quantities.

A still further object of this invention is to provide an improved thickness gauge capable of measuring the thickness of sheets at higher accuracies than conventional apparatus in which the informations recorded on recording papers are read.

According to this invention these and other objects can be accomplished by providing a thickness gauge of the type wherein the thickness of a sample or a sheet to measured interposed between a source of radiation and a radiation detector is measured by detecting the amount of the radiations which have been transmitted through the sample and attenuated functionally in accordance with the radiation absorption characteristic and the thickness of the sample, wherein the thickness gauge comprises means for transmitting a radiation flux through a reference sheet utilized for calibration purposes and having a thickness manifesting a radiation absorption which is equivalent to that of the sample having a nominal thickness which has been compensated for the difference in the radiation absorption characteristics of the reference sheet and the sample, means for detecting the amount of the radiations transmitting through the reference sheet and the sample, memory means for storing the output of the detecting means when the reference sheet is irradiated with the radiation flux, and operator means in which the output of the detecting means when the sample is irradiated with the radiation flux is substituted in a term of an equation representing the variation in the thickness determined by the content of the memory means and the radiation absorption function of the reference sheet so as to produce an output signal representing the thickness of the sample.

BRIEF DESCRIPTION OF THE DRAWING

Further objects and advantages of the invention together with the organization thereof can be more fully understood from the following detailed description taken in conjunction with the accompanying drawing in which.

DESCRIPTION OF THE PREFERRED EMBODIMENT

Figure 1:
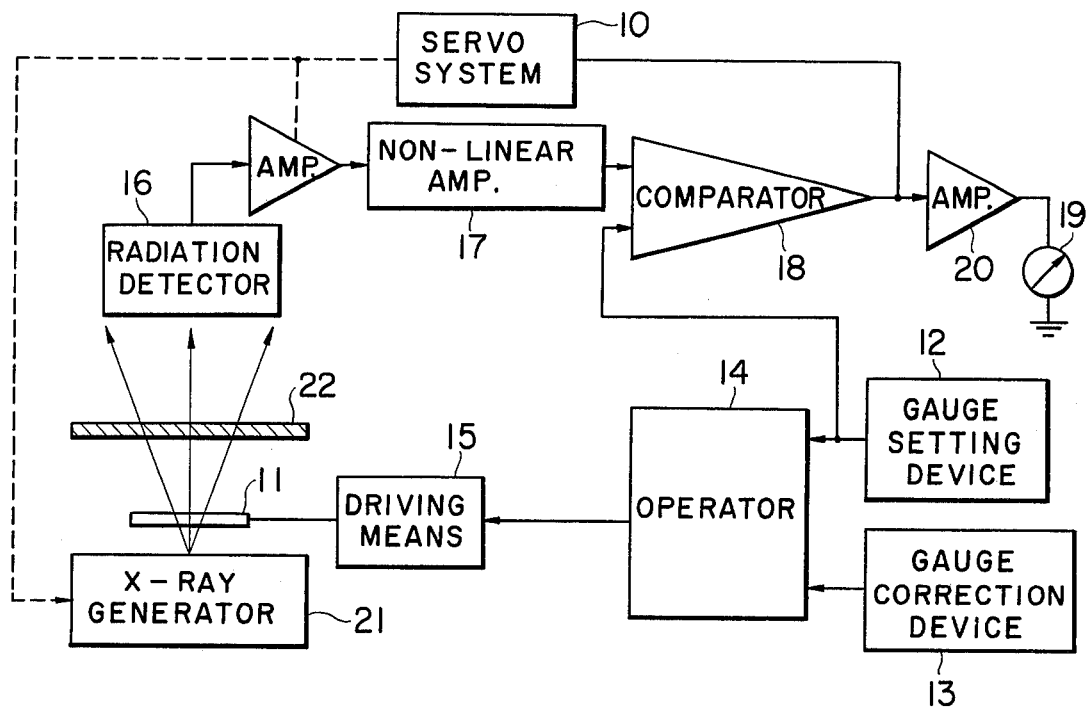
FIG. 1 is an electric block diagram of a prior art radiation thickness gauge.
Figure 2:
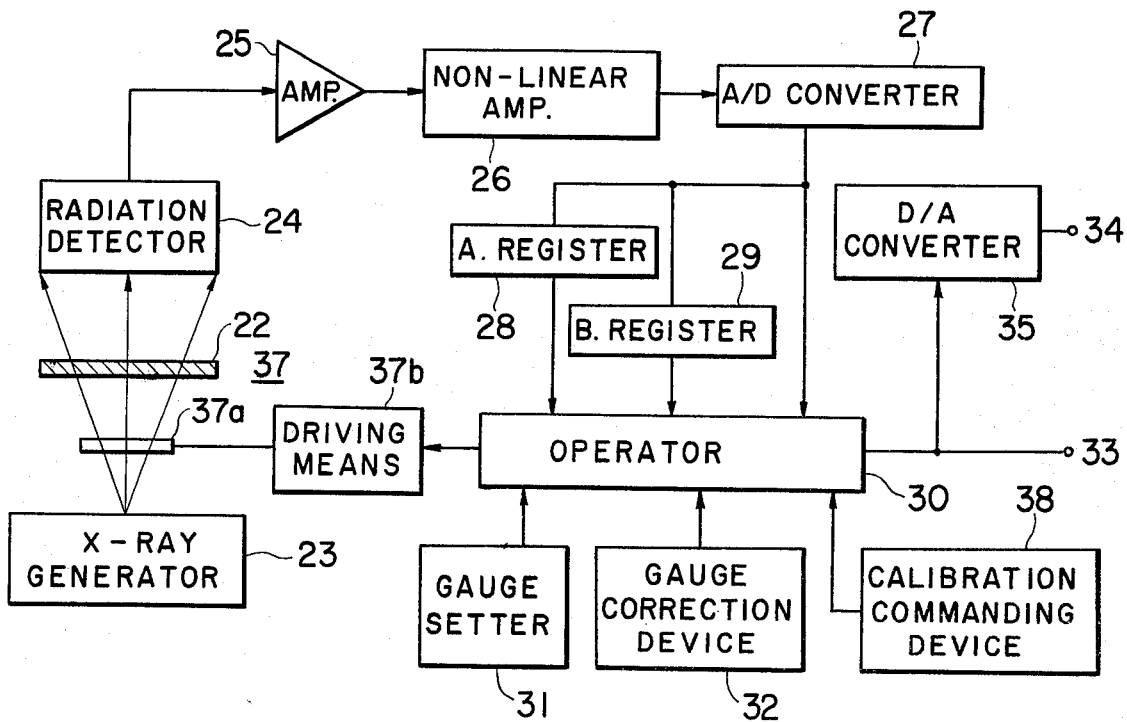
FIG. 2 is an electric block diagram of a novel radiation thickness gauge embodying the invention.

In a preferred embodiment of this invention illustrated in FIG. 2, the output of a radiation detector 24 which is disposed to receive the X-rays generated by a X-ray generator 23 and converts the received X-rays into an electric signal is applied to a nonlinear amplifier 26 through an amplifier 25. The output of the non-linear amplifier 26 is coupled to the inputs of A register 28, B register 29 and an operator 30 via an analogue-digital converter 27. The operator 30 is applied with the output from a setter 31 which produces a thickness set signal corresponding to the thickness of a sheet to be measured and the output of a gauge correction device 32 in addition to the outputs from registers 28 and 29 and the analogue-digital converter 27, so that the operator 30 performs an operation in accordance with an equation that determines a reference sheet having an amount of radiation absorption equivalent to that of the sheet to be measured having a nominal thickness. The output from the operator 30 is applied to means 37 for driving the reference sheet 37a. Further, in response to the output from registors 28 and 29 and analogue-digital converter 27, the operator 30 determines the thickness of the sheet to be measured, and the result of the operation, that is a digital signal corresponding to the thickness of the sheet to be measured is applied directly to a first output terminal 33 and to a second output terminal 34 through a digital-analogue converter 35. The means 37 for driving the reference sheet 37a comprises a plurality of reference sheets 37a made of a prescribed material and having different thicknesses, and means 37b for inserting a reference sheet corresponding to the output from the operator 30 into the X-ray flux generated by the X-ray generator 23 at a point between the same and the radiation detector 24. There is also provided means 38 for applying a calibration command signal to the operator 30.

The thickness gauge shown in FIG. 2 operates as follows: The characteristic of the non-linear amplifier 26 is adjusted such that the radiation absorption function of the reference sheets 37a can be expressed by an equation of the first degree. Then, the nominal thickness $x_o$ and a value N representing the material of the sheet 22 to be measured are set in the gauge setting device 31 and the gauge correction device 32, respectively for the purpose of compensating for the difference in the materials of the reference sheet 37a and the sheet 22 to be measured. The state of the operator 30 is changed to the calibration state by a calibration commencing signal from the calibration commanding device 38, thus inserting across the X-ray flux a reference sheet $Nx_o$ having an apparent thickness manifesting a quantity of radiation absorption equivalent to that of the sheet to be measured having the nominal thickness. A signal $Vx_1$ produced by the analogue-digital converter 27 at that time is stored in A register 28. Another reference sheet $\alpha Nx_o$ having an apparent thickness and manifesting a quantity of radiation absorption which is equivalent to the product of the nominal thickness $x_o$ of the sheet to be measured which has been set in the gauge setting device 31 and a deviation from the nominal thickness is inserted across the X-ray flux, and the signal $Vx_2$ produced by the analogue-digital converter 27 at this time is stored in the B register 29 for calibrating the thickness gauge. After calibration, the sheet 22 to be measured is substituted for the reference sheet 37a. Under these conditions the following equation 1 holds based on the contents of the A and B registers 28 and 29.

$$\frac{x - Nx_o}{\alpha Nx_o - Nx_o} = \frac{Vx - Vx_1}{Vx_2 - Vx_1} \tag{1}$$

By modifying this equation, we obtain $$x = Nx_o + \frac{Vx - Vx_1}{Vx_2 - Vx_1}(\alpha Nx_o - Nx_o) \tag{2}$$

By substituting the output of the analogue-digital converter which is produced when a sheet to be measured is inserted across the radiation flux for $Vx$ in equation 2, we can determine the thickness $x$ of the sheet to be measured since the values of $N$, $x_o$, $Vx_1$, $Vx_2$ and $Vx$ are known. According to this invention this calculation is performed by the operator 30 thereby producing a digital quantity of the thickness of the sheet to be measured on the first output terminal 33 and an analogue quantity of the thickness of the sheet to be measured on the second output terminal 34.

Actually, the ratio between the thickness of the sheet to be measured and the thickness of the reference sheet is given by the equation 2 and by correcting the resulting value with a factor $N$ that represents the difference between the absorption characteristics of the sheet to be measured and of the reference sheet, equation 2 is modified as follows $$x = x_o + \frac{Vx - Vx_1}{Vx_2 - Vx_1}(\alpha x_o - x_o) \tag{3}$$

This equation also gives the thickness of the sheet to be measured.

To obtain the deviation $\Delta x$ of the thickness from a given value $x_o$, since $$\Delta x = x - x_o$$

we obtain $$\Delta x = \frac{Vx - Vx_1}{Vx_2 - Vx_1}(\alpha x_o - x_o)$$

This operation can also be made in the operator 30.

Since a reference sheet having a thickness manifesting the same amount of absorption as the sheet to be measured having the nominal thickness is interposed across the radiation flux and since the non-linear amplifier 26 has been adjusted such that the radiation absorption characteristics of the reference sheet are expressed by a function of an equation of the first order it is possible to determine the thickness of the sheet to be measured by setting up an equation by utilizing the function adapted to convert the radiation absorption characteristics of the reference sheet into the equation of the first order and the output signal of the analogue-digital converter 27 which is produced when a reference sheet manifesting the same amount of radiation absorption as that of the sheet to be measured and having the nominal thickness is used and by substituting the digital signal produced by the analogue-digital converter and representing the thickness of the sheet to be measured for a term representing the variation in the thickness in said equation.

Thus, the operator or computer performing such calculation produces an output in the form of a digital quantity which directly represents the thickness of the sheet to be measured.

Thus, the invention provides an improved radiation thickness gauge in which the output of an analogue-digital converter which is produced when a sample to be measured is inserted across the radiation flux is substituted in a term of an equation which represents the variation in the thickness determined by the output of the analogue-digital convertor which is produced when a reference sheet manifesting the same amount of the radiation absorption as the sample having the nominal thickness is inserted across the radiation flux and a function determined by the radiation absorption characteristic of the reference sheet and the equation is operated in an operator thus providing a digital output directly representing the thickness of the sample. With this thickness gauge it is unnecessary to use a servo-system for calibration and since the thickness is determined essentially by digital operations it is possible to eliminate measuring errors caused by drifts. Furthermore, as the thickness gauge is calibrated by the same amount of radiation absorption as that of the sample it is possible to improve the accuracy and stability of the measurement by eliminating error components caused by the differences in the radiation energy and in the intensity of the radiation at the times of measurement and calibration. As a result, the handling of the thickness gauge is greatly simplified because it is only necessary to set the calibration signal, the desired thickness and the thickness correction at the time of calibrating the thickness gauge. Further, as the thickness of the sample is expressed directly as a digital quantity it is possible to decrease the reading error. As the deviation of the thickness is determined by an operation the measurement accuracy can be made more accurate than the conventional apparatus in which the information recorded on a recording paper of a recording meter is read.

Although in the foregoing embodiment a non-linear amplifier was used to produce a signal proportional to the thickness of the sample, it should be understood that the invention is not limited to such specific arrangement and that such output can also be produced by using an operator or computer which performs functional operations.

We claim:

1. In a thickness gauge of the type wherein the thickness of a sample to be measured interposed between a source of radiations and a radiation detector is measured by detecting the amount of the radiations which have been transmitted through said sample and attenuated functionally in accordance with the radiation absorption characteristic and the thickness of said sample, the improvement which comprises means for transmitting a radiation flux through a reference sheet utilized for calibration purposes and having a thickness manifesting a radiation absorption which is equivalent to that of the sample having a nominal thickness which has been compensated for the difference in the radiation absorption characteristics of said reference sheet and said sample, means for detecting the amount of the radiations transmitting through said reference sheet and said sample, memory means for storing the output of said detecting means when said reference sheet is irradiated with the radiation flux, and operator means in which the output of said detecting means when said sample is irradiated with the radiation flux is substituted for a term of an equation representing the variation in the thickness determined by the content of said memory means and the radiation absorption function of said reference sheet so as to produce an output signal representing the thickness of said sample.

2. The thickness gauge according to claim 1 which further comprises driving means for the reference sheet which contains a plurality of reference sheets having different thicknesses and functions in response to the output of said operator means for selecting one of the reference sheets and for inserting the selected reference sheet in the path of the radiation flux.

3. The thickness gauge according to claim 1 which further comprises a non-linear amplifier and an analogue-digital converter which are connected in series between the output of said detecting means and the input of said memory means.

4. The thickness gauge according to claim 3 wherein the equation is expressed as follows $$x = x_o + \frac{Vx - Vx_1}{Vx_2 - Vx_1}(\alpha x_o - x_o)$$

where $x$ repesents the thickness of said sample, $x_o$ the nominal thickness of the sample $Vx$ the output of the analogue-digital converter when the sample is inserted, $Vx_1$ the output of the analogue-digital converter when a reference sheet is interposed which has been compensated for the difference in the materials of the sample and the reference sheet, $Vx_2$ the output of the analogue-digital converter when another reference sheet is interposed which has been compensated for the deviation from the nominal thickness of the sample, and $\alpha$ the deviation from the nominal thickness of the sample.

5. The thickness gauge according to claim 1 which further comprises an analogue-digital converter adapted to convert the output of said detecting means into a digital quantity, and wherein said memory means comprises a first register for storing the output of said analogue-digital converter when a reference sheet is interposed which has been compensated for the difference in the materials of the sample and the reference sheet and a second register for storing the output of the analogue-digital converter when another reference sheet is interposed which has been compensated for the deviation from the nominal thickness of the sample.

6. The thickness gauge according to claim 1 which further comprises a digital-analogue converter connected to the output of said operator means for converting the digital output thereof into an analogue quantity.

7. The thickness gauge according to claim 1 which further comprises a calibration commanding device which applies a calibration commencing signal to said operator means for changing the state thereof to the calibration state.

8. The thickness gauge according to claim 1 which further comprises a gauge setter connected to said operator means for setting therein a desired gauge of said sample.

9. The thickness gauge according to claim 1 which further comprises a gauge correction device connected to said operator means for correcting the difference in the material comprising said sample and said reference sheet.

* * * * *